(12) United States Patent
Lindberg

(10) Patent No.: US 10,256,379 B2
(45) Date of Patent: Apr. 9, 2019

(54) OPTOELECTRONIC COMPONENT AND METHOD FOR PRODUCING AN OPTOELECTRONIC COMPONENT

(71) Applicant: OSRAM Opto Semiconductors GmbH, Regensburg (DE)

(72) Inventor: Gudrun Lindberg, Bad Abbach (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 0 days.

(21) Appl. No.: 15/579,090

(22) PCT Filed: May 25, 2016

(86) PCT No.: PCT/EP2016/061806
§ 371 (c)(1),
(2) Date: Dec. 1, 2017

(87) PCT Pub. No.: WO2016/193098
PCT Pub. Date: Dec. 8, 2016

(65) Prior Publication Data
US 2018/0175260 A1 Jun. 21, 2018

(30) Foreign Application Priority Data
Jun. 2, 2015 (DE) .......... 10 2015 108 736

(51) Int. Cl.
*H01L 33/56* (2010.01)
*H01L 33/54* (2010.01)
(Continued)

(52) U.S. Cl.
CPC .............. *H01L 33/56* (2013.01); *C07F 1/00* (2013.01); *C07F 1/02* (2013.01); *C07F 3/00* (2013.01);
(Continued)

(58) Field of Classification Search
CPC ......... H01L 33/56; H01L 33/48; H01L 33/44; H01L 33/54; H01L 33/62; H01B 3/30;
(Continued)

(56) References Cited

U.S. PATENT DOCUMENTS 4,821,148 A * 4/1989 Kobayashi ............ H01L 23/293
174/529
7,777,352 B2 * 8/2010 Mahler ............... H01L 23/3142
257/666

(Continued)

FOREIGN PATENT DOCUMENTS

| CN | 102516314 A | 6/2012 |
| DE | 102005061828 A | 1/2007 |

(Continued)

OTHER PUBLICATIONS

Crudden, C.M. et al., "Ultra Stable Self-Assembled Monolayers of N-Heterocyclic Carbenes on Gold," Nature Chemistry, Published Online Mar. 23, 2014, 8 pages.

*Primary Examiner* — Dao H Nguyen
(74) *Attorney, Agent, or Firm* — Slater Matsil, LLP

(57) ABSTRACT

An optoelectronic component and a method for producing an optoelectronic component are disclosed. In an embodiment an optoelectronic component includes at least one metallic surface, a contacted optoelectronic semiconductor chip configured to emit radiation and a protective layer arranged on the at least one metallic surface, wherein the protective layer comprises a protective material of at least one N-heterocyclic carbene, and wherein a covalent bond is formed between the protective material and the at least one metallic surface.

14 Claims, 3 Drawing Sheets

(51) Int. Cl.
*H01L 33/60* (2010.01)
*C07F 1/00* (2006.01)
*H01L 23/49* (2006.01)
*H01B 3/30* (2006.01)
*H01L 33/44* (2010.01)
*C07F 1/02* (2006.01)
*C07F 3/00* (2006.01)
*C07F 3/02* (2006.01)
*C07F 5/00* (2006.01)
*C07F 5/06* (2006.01)
*H01L 33/62* (2010.01)
*H01L 33/48* (2010.01)
*H01L 23/00* (2006.01)

(52) U.S. Cl.
CPC .............. *C07F 3/02* (2013.01); *C07F 5/00* (2013.01); *C07F 5/062* (2013.01); *H01B 3/30* (2013.01); *H01L 33/44* (2013.01); *H01L 33/54* (2013.01); *H01L 33/62* (2013.01); *H01L 24/48* (2013.01); *H01L 33/48* (2013.01); *H01L 2224/48091* (2013.01); *H01L 2224/48106* (2013.01); *H01L 2224/48247* (2013.01); *H01L 2224/48465* (2013.01); *H01L 2224/8592* (2013.01); *H01L 2924/12041* (2013.01); *H01L 2933/005* (2013.01); *H01L 2933/0066* (2013.01)

(58) Field of Classification Search
CPC .... C07F 5/00; C07F 5/062; C07F 3/00; C07F 3/02; C07F 1/00; C07F 1/02
USPC ... 257/98, 99, 676, 686, 693, 784, 787, 790, 257/E33.056, E33.067, E33.072, E23.025, 257/E23.116, E23.119, E23.127, E21.504, 257/E21.506
See application file for complete search history.

(56) References Cited

U.S. PATENT DOCUMENTS

| | | | |
|---|---|---|---|
| 8,723,198 B2 | 5/2014 | Brunner et al. | |
| 9,203,042 B2 | 12/2015 | Schmid et al. | |
| 9,219,172 B2 | 12/2015 | Müller et al. | |
| 9,508,903 B2* | 11/2016 | Fehrer | H01L 24/24 |
| 2010/0230696 A1 | 9/2010 | Fukunaga | |
| 2011/0163345 A1* | 7/2011 | Fukunaga | H01L 21/565 |
| | | | 257/98 |
| 2013/0277816 A1* | 10/2013 | Zhang | H01L 21/56 |
| | | | 257/676 |
| 2013/0313604 A1 | 11/2013 | Engl et al. | |
| 2014/0275555 A1 | 9/2014 | Johnson et al. | |
| 2014/0291658 A1 | 10/2014 | Müller et al. | |
| 2016/0199875 A1* | 7/2016 | Crudden | B32B 15/04 |
| | | | 427/249.1 |

FOREIGN PATENT DOCUMENTS

| | | |
|---|---|---|
| DE | 102008030926 A1 | 1/2009 |
| DE | 102009023350 A1 | 12/2010 |
| DE | 102009058796 A1 | 6/2011 |
| DE | 102011016935 A1 | 10/2012 |
| DE | 102011113428 A1 | 3/2013 |
| WO | 2009028156 A1 | 3/2009 |
| WO | 2015024120 A | 2/2015 |
| WO | 2015044529 A1 | 4/2015 |

\* cited by examiner

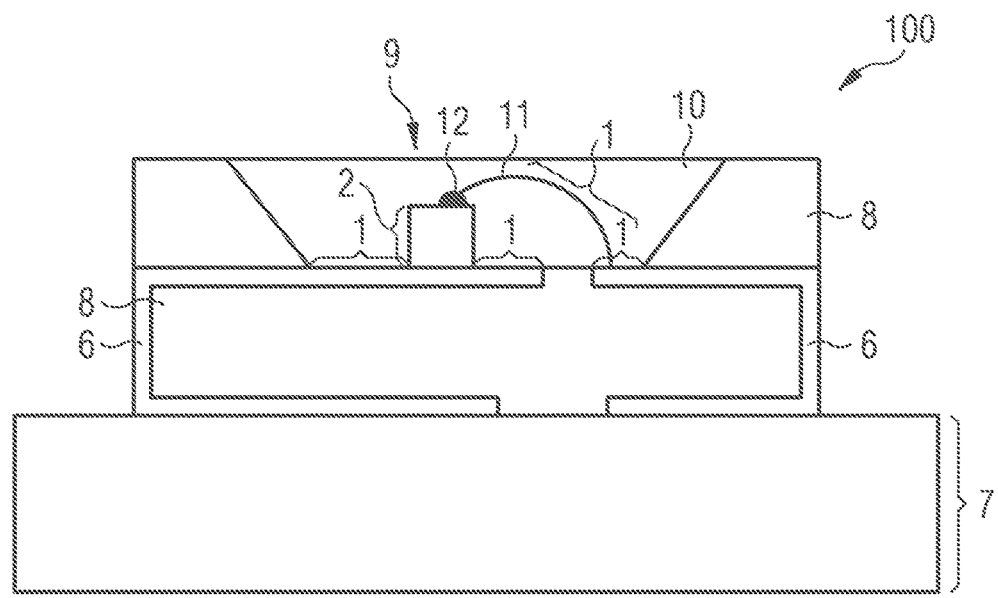
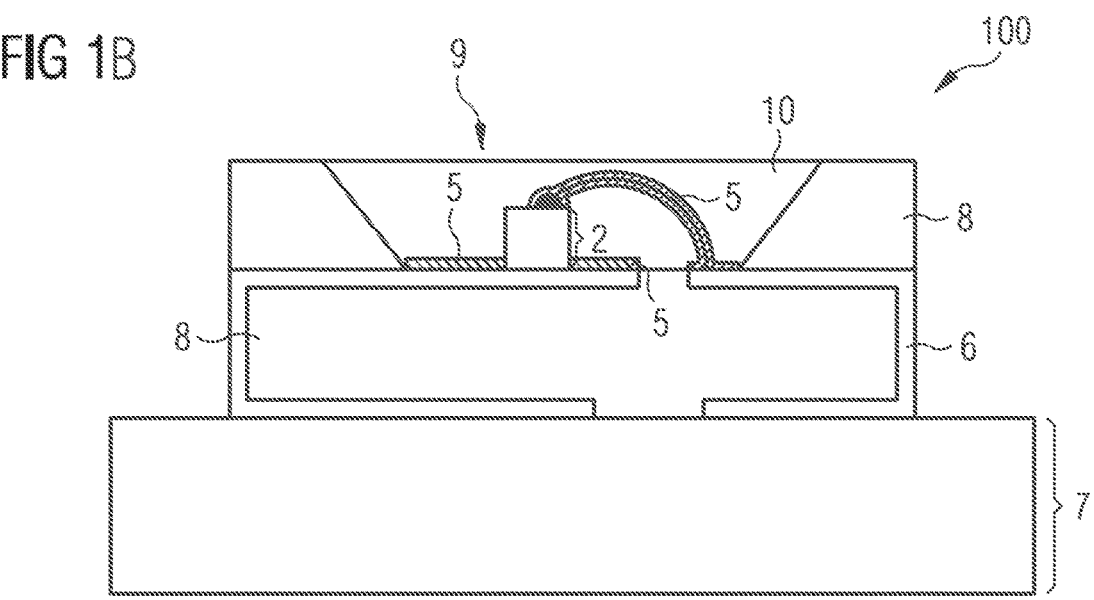

OPTOELECTRONIC COMPONENT AND METHOD FOR PRODUCING AN OPTOELECTRONIC COMPONENT

This patent application is a national phase filing under section 371 of PCT/EP2016/061806, filed May 25, 2016, which claims the priority of German patent application 10 2015 108 736.7, filed Jun. 2, 2015, each of which is incorporated herein by reference in its entirety.

TECHNICAL FIELD

The invention relates to an optoelectronic component. Furthermore, the invention relates to a method for producing an optoelectronic component.

BACKGROUND

Metallic surfaces of optoelectronic components often show corrosion due to gases acting in a highly corrosive manner which get into the optoelectronic component and thus can come into contact with the metallic surfaces. This can lead to an undesired failure of the component.

SUMMARY OF THE INVENTION

Embodiments of the invention provide a stable optoelectronic component. Further embodiments provide a long-lasting optoelectronic component.

In at least one embodiment, the optoelectronic component comprises at least one metallic surface. The optoelectronic component includes a contacted optoelectronic semiconductor chip. The contacted optoelectronic semiconductor chip is configured to emit radiation. The optoelectronic component includes a protective layer. The protective layer is arranged on the at least one metallic surface. The protective layer includes a protective material of at least one N-heterocyclic carbene. A covalent bond is formed between the protective material and the at least one metallic surface.

It would also be conceivable to use inexpensive thiol-based self-assembly monolayers (SAM) as protective material instead of an N-heterocyclic carbene as protective material. When using thiol-based SAMs, however, a significantly reduced heat resistance and chemical resistance have to be expected.

According to at least one embodiment, the optoelectronic component is a light-emitting diode, LED for short. The optoelectronic component in particular comprises a contacted optoelectronic semiconductor chip. The semiconductor chip then is preferably configured to emit blue light or white light.

It is to be noted at this point, that not only finished components such as, for example, light-emitting diodes (LEDs) or laser diodes are addressed with the term "optoelectronic component", but also substrates and/or semiconductor layers, so that, e.g., already a composite of a copper layer and a semiconductor layer can represent a component and form a part of a superior second component, in which electrical connections are present in addition, for example.

According to at least one embodiment, the optoelectronic component comprises a contacted optoelectronic semiconductor chip. The semiconductor chip includes a semiconductor layer sequence. The semiconductor layer sequence of the semiconductor chip is based preferably on a III-V-compound semiconductor material. The semiconductor material is preferably a nitride compound semiconductor material such as $Al_n In_{1-n-m} Ga_m N$ or also a phosphide compound semiconductor material such as $Al_n In_{1-n-m} Ga_m P$, with in each case $0 \leq n \leq 1$, $0 \leq m \leq 1$ and $n+m \leq 1$. The semiconductor material can as well be $Al_x Ga_{1-x} As$, with $0 \leq x \leq 1$. Here, the semiconductor layer sequence can include dopants as well as additional constituents. For the sake of simplicity, however, only the substantial constituents of the crystal lattice of the semiconductor layer sequence, i.e., Al, As, Ga, In, N or P, are indicated, even if these can be partly displaced and/or supplemented by small amounts of other substances.

The semiconductor layer sequence includes an active layer with at least one p-n-junction and/or one or multiple quantum well structures. During operation of the semiconductor chip, an electromagnetic radiation is generated in the active layer. A wavelength or the wavelength maximum is preferably in the ultraviolet and/or visible spectral range, in particular at wavelengths between 420 nm and 680 nm inclusive, for example, between 440 nm and 480 nm inclusive.

The optoelectronic semiconductor chip is contacted. Here and in the following, this means that the optoelectronic semiconductor chip comprises at least two connecting points, in particular a p-connection contact and an n-connection contact, which electrically contact the semiconductor layer sequence. In other words, the optoelectronic component comprises a semiconductor chip which is operational. The semiconductor chip is configured to emit radiation. In particular, the active region of the semiconductor layer sequence is configured to emit radiation.

According to at least one embodiment, the optoelectronic component includes at least one metallic surface. In particular, the optoelectronic component can include multiple metallic surfaces. Metallic surfaces mean all surfaces made of metal or at least an alloy which is able to form a covalent bond with the protective material.

According to at least one embodiment, the metallic surface is selected from a group including a surface of a first metallic connection contact, of a second metallic connection contact, of a lead frame, of a bond pad and a bond wire. In particular, the metallic surface includes at least one metal or an alloy, which is selected from: silver, aluminum, cadmium, barium, indium, magnesium, calcium, lithium, gold or combinations thereof. In particular, the metallic surface can include an alloy or consist thereof, for example of: Ag:Mg, Ag:Ca, Mg:A.

According to at least one embodiment, the optoelectronic component comprises a protective layer. The protective layer is arranged at least on the one metallic surface or on multiple metallic surfaces. As used herein, the fact that a layer or an element is arranged or applied "on" or "over" another layer or another element can mean that the one layer or the one element is directly arranged in direct mechanical and/or electrical contact with the other layer or the other element. Furthermore, it can also mean that the one layer or the one element is indirectly arranged on or over the other layer or the other element. Here, further layers and/or elements can be arranged between the one and the other layer or between the one and the other element.

According to at least one embodiment, the protective layer covers the metallic surface in a form-fit manner. Here, "form-fit" means that the protective layer adapts to the design or shape of the metallic surface. Here, in particular a direct mechanical contact between the metallic surface and the protective layer is present. If the metallic surface is, for example, a bond wire, the protective layer coats the wire from all sides. Thus, it can be prevented that corrosive gases get to the bond wire and corrode it. Thus, the service life of the component can be prolonged.

According to at least one embodiment, the protective layer includes a protective material of at least one N-heterocyclic carbene. In particular, the protective layer consists of a protective material of at least one N-heterocyclic carbene. Alternatively, instead of a N-heterocyclic carbene, also a mixture of multiple N-heterocyclic carbenes can be present as protective material in the protective layer of the optoelectronic component.

According to at least one embodiment, the protective material consists of an N-heterocyclic carbene. In particular, the N-heterocyclic carbene is selected from a group including

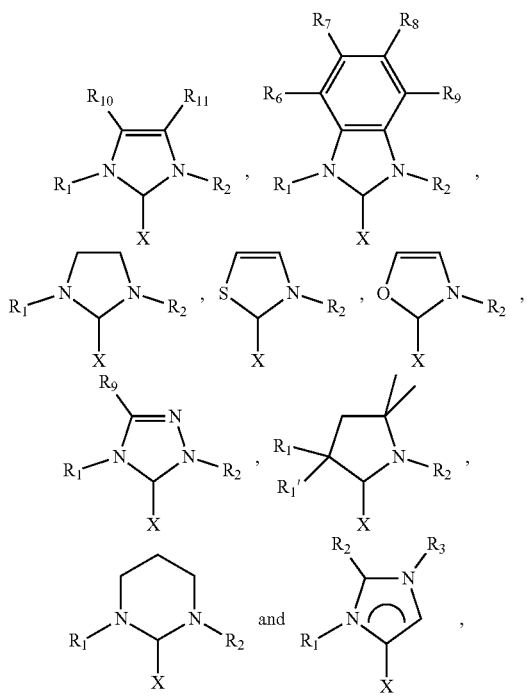

wherein $R_1$, $R_1'$, $R_2$, $R_3$, $R_4$, $R_5$, $R_6$, $R_7$, $R_8$, $R_9$, $R_{10}$ and $R_{11}$ are selected independently from one another of hydrogen, alkyl groups, alkoxy groups, groups with amines, amides, ester, carbonates, substituted od unsubstituted aromatic compounds, substituted or unsubstituted hetero-aromatic compounds, halogens, pseudo-halogens, and combinations thereof. The —X illustrated in the individual formulas shows in each case a covalent bond to the at least one metallic surface X.

According to at least one embodiment, the protective material is selected from:

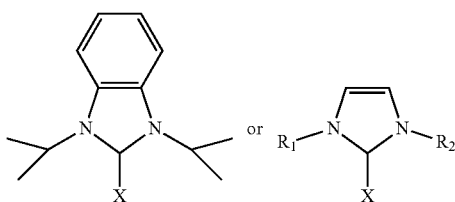

wherein $R_1$ and $R_2$ are in each case an alkyl-substituted phenyl, or

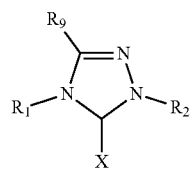

wherein $R_1$, $R_2$ and $R_9$ is in each case a phenyl,
wherein —X is a covalent bond to the metallic surface (1).

According to at least one embodiment, the protective material is

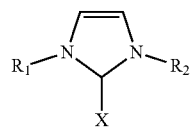

wherein $R_1$ and $R_2$ is in each case 2,4,6-trimethylphenyl or 1,3-bisisopropylphenyl.

In particular, the protective layer consists of or comprises the N-heterocyclic carbene: 1,3-bisisopropyl-2H-benzimidazole-2-ylidene.

According to at least one embodiment, the protective layer is formed as a self-assembled monolayer (SAM for short). In particular, the monolayer has a layer thickness of equal to or smaller than 10 nm, in particular equal to or smaller than 5 nm, in particular equal to or smaller than 1 nm, for example, 0.4 nm. Here, a layer of atoms or molecules on a metallic surface is referred to as monolayer, wherein the layer thickness is only one atom or one molecule.

According to at least one embodiment, the protective material is free of sulfur. This means that the N-heterocyclic carbenes do not include any sulfur atoms. As a result, no covalent bond of the N-heterocyclic carbene to the metal surface develops via a sulfur atom.

According to at least one embodiment, the protective material includes a side chain or side chains which include sulfur. The covalent bond of the N-heterocyclic carbene to the metallic surface is affected via a carbon atom of the carbene. In other words, no covalent bond of the N-heterocyclic carbene to the metallic surface is effected via a sulfur atom of the side chain or side chains. In particular, the covalent bond of the N-heterocyclic carbene to the metallic surface is effected via a carbon, in particular via a carbon atom. In other words, a covalent bond forms between a metal of the metallic surface and the carbon of the N-heterocyclic carbene. In particular, the covalent bond is effected via the carbon atom of the carbene in the five-membered ring, which is arranged between neighboring nitrogen atoms. In particular, the covalent bond is effected via the non-binding electron pair of the divalent carbene carbon, which is in the direct vicinity between two neighboring nitrogen atoms. The reactive carbene can be stabilized by the neighboring nitrogen atoms, which function as donor substituents (ylide form).

Compared to N-heterocyclic carbenes, carbenes are instable, very reactive compounds of a divalent carbon with electron sextet. The increased stability of N-heterocyclic carbenes compared to other carbenes is achieved especially by the -I-effect of the neighboring electronegative substituents, as well as the donor function thereof via the free electron pair in the unoccupied p-orbital of the carbene carbon. N-heterocyclic carbenes are in particular of the Arduengo type. Besides nitrogen, sulfur or oxygen or phosphor can also stabilize the carbene. N-heterocyclic carbenes having an imidazole basic structure are additionally stabilized by the π-system forming by means of mesomerism effects. As a result, in particular a protective layer can be provided, which is stable and additionally protects the optoelectronic component against environmental influences, for example, corrosion.

According to at least one embodiment, the protective layer is diffusion-resistant against corrosive gases. Here and in the following, "diffusion-resistant" means that the protective layer has a low diffusion coefficient for gases, in particular for corrosive gases, for example, hydrogen sulfide. Due to the low diffusion coefficient of the protective layer, hydrogen sulfide may actually escape from a potting material present in the component which includes rubber material vulcanized with sulfur, but this hydrogen sulfide does not diffuse through the protective layer and thus does not lead to corrosion of metallic surfaces of the optoelectronic component. As a result, the persistence and the stability of the optoelectronic component can be increased and undesired component failure can be prevented.

According to at least one embodiment, all metallic surfaces of the optoelectronic component are covered with the protective layer in a form-fit manner. Here, "form-fit" means that the protective layer coats the metallic surfaces or is arranged downstream thereon, though without interfering the function thereof. That means, for example, that an optoelectronic component can emit radiation despite a present protective layer and current can flow. Here, "all metallic surfaces" means in particular metallic surfaces of connection points, metallic surfaces of lead frames, bond wires and/or bond pads.

According to at least one embodiment, the contacted optoelectronic semiconductor chip is arranged in a housing. The housing comprises a recess, in which the contacted optoelectronic semiconductor chip is arranged. The optoelectronic component comprises metallic surfaces, which are in particular at least metallic surfaces of a bond pad, a bond wire and/or a lead frame or includes these. The protective layer is applied then on to the metallic surfaces of the bond pad, the bond wire and/or the lead frame. In particular, the protective layer covers the optoelectronic component within the recess in a form-fit manner. The recess can alternatively or additionally be potted with a potting material. As a potting material, silicone is appropriate, in particular silicone-based materials such as, for example, methyl-substituted silicone, phenyl-substituted silicone or methylphenyl-substituted silicone.

Silicone materials as a potting material provide the advantage that they are thermally stable and have a high optical transparency. However, compared to epoxide materials, silicone materials have a certain permeability for gases, in particular for gases acting corrosive. This plays a role especially during operation of optoelectronic components when an outgassing of aggressive substances from otherwise present materials occurs at increased system temperatures.

The inventor has found now that the use of a protective layer on metallic surfaces of an optoelectronic component allows preventing interference, in particular corrosion by diffusion of gases acting corrosive. With the help of the protective layer, which includes in particular at least one N-heterocyclic carbene, in particular a SAM of a N-heterocyclic carbene, the corrosion of metallic surfaces can be prevented, and thus an accelerated component aging can be actively obviated. This produces a long-term stability of the component.

In particular, the protective layer is a layer permanently remaining in the component. Therefore, it is important that the protective layer forming on the metallic surface, in particular the SAM, is a stable system. This stable system can be generated by the covalent formation between the protective layer and the metallic surface.

The use of a protective layer of an N-heterocyclic carbene allows increasing the overall component stability. Furthermore, the optoelectronic component can thereby be employed, for example, in moisture affected areas. The service life of the optoelectronic component can be increased. There is no longer need for the use of expensive precious metals such as gold, for the reduction of the layer thickness, for example. This saves costs. Due to a diffusion-resistant protective layer, the diffusion coefficient of the encapsulation or of the potting or the composition thereof is no longer a decisive factor, so that each encapsulation or each potting may be used independently of the diffusion coefficient thereof. Furthermore, the use of a protective layer allows preventing failures of the optoelectronic component caused by corrosive materials. On the other hand, also gas-permeable potting materials can be used, which could not be used in uncoated metallic surfaces due to the corrosion. Thus, epoxide can be used as potting material, for example.

The invention further relates to a method for producing an optoelectronic component. Preferably, the method produces the optoelectronic component. Here, the same definitions and configurations of the optoelectronic component apply for the method for producing the optoelectronic component and vice versa.

According to at least one embodiment, the method includes the following method steps: (A) Providing a contacted optoelectronic semiconductor chip, (B) Providing at least one metallic surface, (C) Applying a protective layer on to the at least one metallic surface, wherein the protective layer, includes or consists of at least one heterocyclic carbene as a protective material, wherein a covalent bond is formed between the at least one N-heterocyclic carbene and the at least one metallic surface, and wherein self-orientation of the at least one N-heterocyclic carbene is effected as a monolayer. In other words, by the bond of the N-heterocyclic carbene to the metallic surface, orientation of the N-heterocyclic carbenes is effected within the protective layer. In particular, orientation of the N-heterocyclic carbenes is effected as a monolayer.

According to at least one embodiment, step C) is effected by means of vapor deposition, in particular physical vapor deposition (PVD) and/or chemical vapor deposition (CVD).

According to at least one embodiment, step C) is effected by means of wet-chemical processes. In particular, all methods are suitable that are suitable for applying an N-heterocyclic carbene from solution. In particular, step C) can be effected by means of spin-coating, printing, dip-coating or spray-coating.

According to at least one embodiment, an additional step D) is effected after step C):

D) Potting the contacted optoelectronic semiconductor chip and the metallic surface coated with the protective layer. Thus, the protective layer becomes a part of the optoelectronic component and remains in the optoelectronic component.

According to at least one embodiment, step D) is effected by means of a potting material of silicone.

BRIEF DESCRIPTION OF THE DRAWINGS

Further advantages, advantageous embodiments and developments result from the exemplary embodiments described in the following in conjunction with the figures.

The figures show in:

FIGS. 1A, 1B and 2 and 3 in each case a schematic side view of an optoelectronic component 100 according to an embodiment, and FIGS. 4A to 4C a schematic detail of a side view of an optoelectronic component 100 according to an embodiment.

Figure 2:
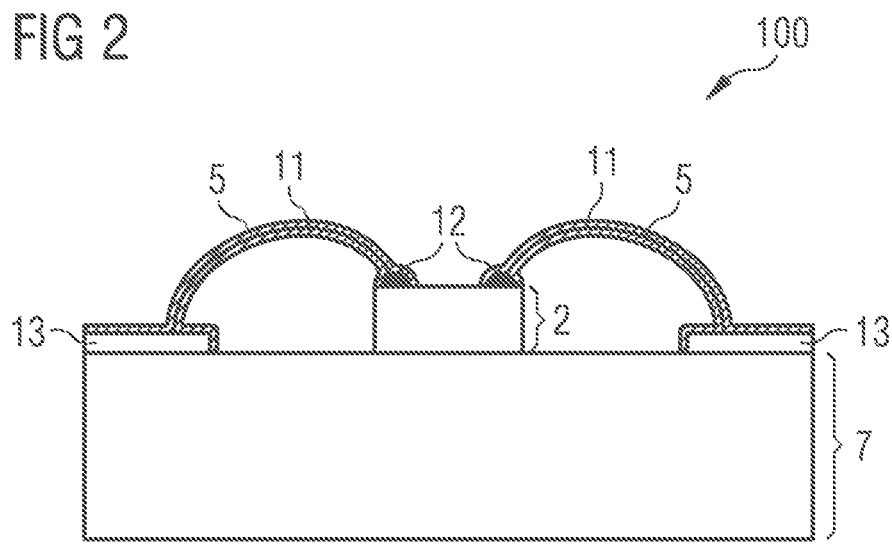

In the exemplary embodiments and figures, like, equivalent or elements acting in the same manner can be denoted with the same reference characters, respectively. The illustrated elements and their size ratios to one another are considered not to be to scale. Rather, for a better illustration and/or a better understanding, individual elements, such as layers, components, devices and regions can be illustrated in an exaggerated size.

DETAILED DESCRIPTION OF ILLUSTRATIVE EMBODIMENTS

FIG. 1A shows a schematic side view of an optoelectronic component 100 according to an embodiment. The optoelectronic component 100 comprises a carrier 7. The carrier 7 can be a printed circuit board (PCB), a ceramic substrate, a circuit board or an aluminum board. A housing 8 is arranged downstream the carrier 7. The housing 8 comprises a lead frame 6. The lead frame 6 comprises electrical connection points, with which a contacted semiconductor chip 2 is electrically connected. The housing 8 comprises a recess 9, within which the contacted semiconductor chip 2 is arranged. The contacted semiconductor chip 2 is arranged on a region of the lead frame 6. The semiconductor chip 2 comprises a bond pad 12 and a bond wire 11, with which the electrical connection via the lead frame 6 is affected. The optoelectronic component 100 comprises metallic surfaces 1. Here, the metallic surfaces 1 are in particular the metallic surfaces, present within the recess 9, of the lead frame 6 as well as of the bond wire 11 and of the bond pad 12. The component 100 may include a protective layer 5 (not shown here, see FIG. 1B).

FIG. 1B is different from FIG. 1A in that the protective layer 5 is applied on to the metallic surfaces 1 of the optoelectronic component 100. In particular, the bond wire 11 is covered with the protective layer 5 in a form-fit manner. Furthermore, the bond pad 12 is enclosed by the protective layer 5 in a form-fit manner. The protective layer 5 is generated in particular after applying the bond wire 11 and the bond pad 12. In particular, the protective layer 5 is generated by means of vapor deposition or wet-chemical processes.

Thus, an optoelectronic component 100 can be provided, which comprises all metallic surfaces 1 covered with the protective layer 5, in particular within the recess 9. The protective layer 5 is in particular diffusion-resistant against gases, in particular corrosive gases, such as hydrogen sulfide. Thus, corrosion of the optoelectronic component 100 can be prevented and thereby the longtime stability of the optoelectronic component 100 can be increased.

FIG. 2 shows a schematic side view of an optoelectronic component 100 according to an embodiment. The optoelectronic component 100 includes a carrier 7. Connection points 13 are arranged downstream of the carrier 7. Furthermore, the contacted semiconductor chip 2 is arranged downstream of the carrier 7. The contacted semiconductor chip 2 comprises two bond pads 12 on the radiation exit surface, which faces away from the carrier 7. The bond pads 12 are in each case connected to the connection points 13 by means of a bond wire 11. The metallic surfaces 1 of the optoelectronic component 100 are covered with the protective layer 5 and enclosed therewith. The optoelectronic component 100 of FIG. 2 is different from the optoelectronic component 100 of FIG. 1B in that the contacting is effected above, i.e., through the radiation exit surface of the contacted semiconductor chip 2.

In addition, the optoelectronic component 100 may comprise a potting 10 (not shown here).

Figure 3:
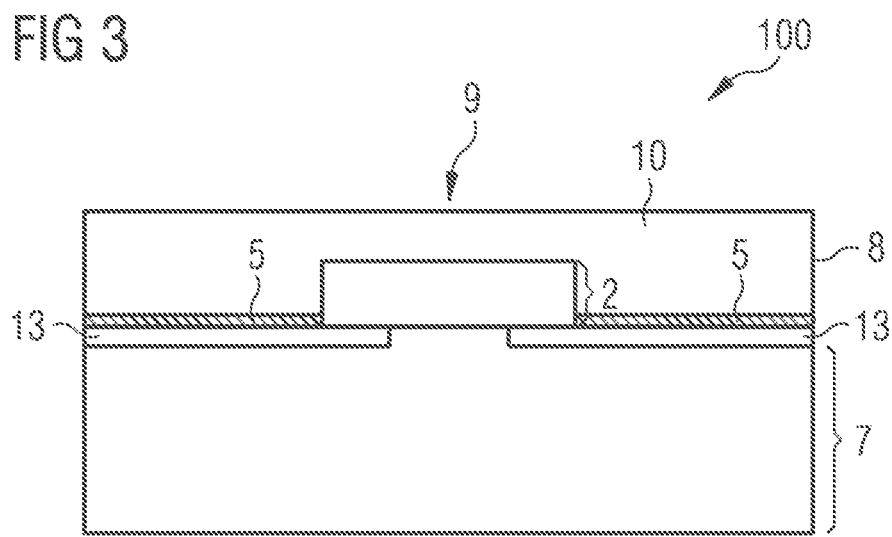

FIG. 3 shows a schematic side view of an optoelectronic component 100 according to an embodiment. The optoelectronic component 100 comprises a carrier 7. The carrier 7 comprises connection points 13. The semiconductor chip 2 is contacted via the connection points 13. The connection points 13 are metallic. The metallic connection points 13 are covered by the protective layer 5 at least in regions. The optoelectronic component 100 can be potted by means of a potting 10.

Figure 4A:
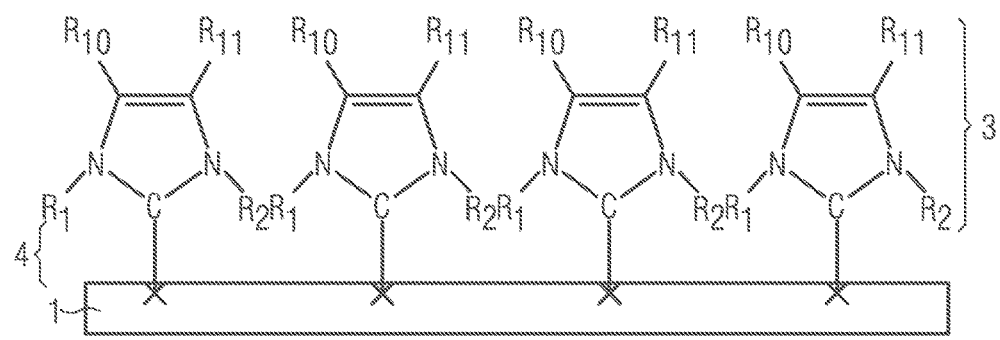
Figure 4B:
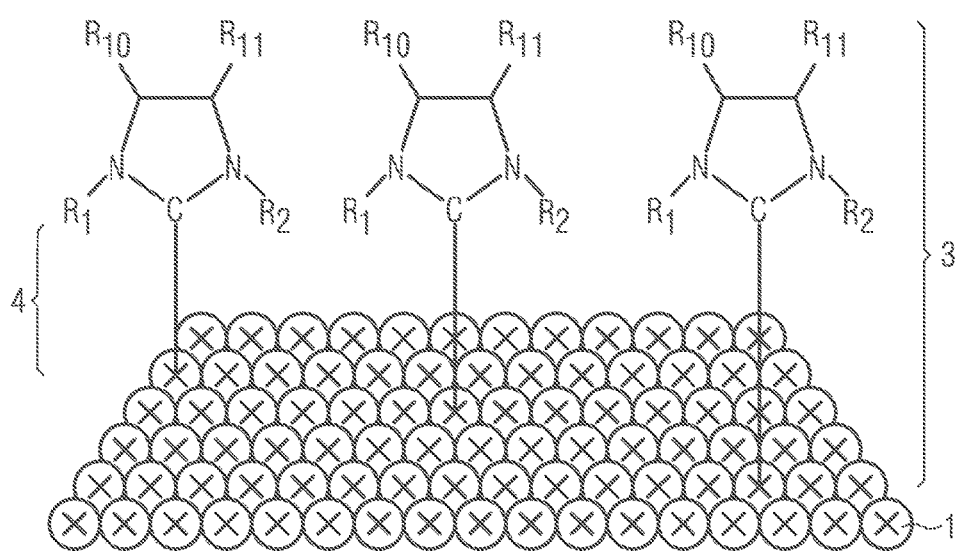
Figure 4C:
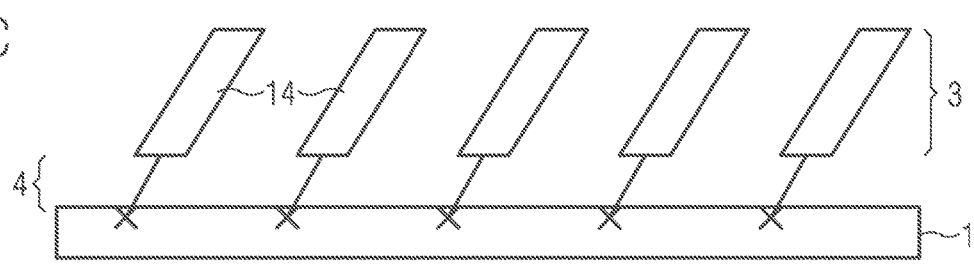

FIGS. 4A to 4C each show a detail of a schematic side view of an optoelectronic component 100 according to an embodiment. FIG. 4A shows the metallic surface 1 which, for example, can be a metallic surface of the bond pad 12, bond wire 11 or connection points of a lead frame 6. The metallic surface 1 comprises atoms, for example, metal atoms X. Via these metal atoms X, the protective material 3, which includes N-heterocyclic carbenes, is connected by a direct covalent bond.

FIG. 4B shows the covalent bond of three N-heterocyclic carbenes to the metallic surface 1. The protective layer 5 forms as self-assembled monolayer. In particular, the self-assembled monolayer has a layer thickness of equal to or less than 1 nm.

FIG. 4C shows a schematic side view of a detail of an optoelectronic component 100 according to an embodiment. FIG. 4C shows the bond of the N-heterocyclic carbene 14 to the metallic surface 1 via the covalent bond. FIG. 4C is to show that the molecules, i.e., the N-heterocyclic carbene molecules, form a self-assembled monolayer, wherein the molecules include longitudinal axes that are inclined toward the metallic surface 1.

The exemplary embodiments and the features thereof described in conjunction with the figures can also be combined according to further exemplary embodiments, even if such combinations are not explicitly shown in the figures. Furthermore, the exemplary embodiments described in conjunction with the figures can comprise additional or alternative features according to the description in the general part.

The invention is not limited to the exemplary embodiments by the description using these exemplary embodiments. Rather, the invention includes any new feature as well as any combination of features which in particular includes each combination of features in the claims, even if this feature or this combination is per se not explicitly stated in the claims or exemplary embodiments.

The invention claimed is:

1. An optoelectronic component comprising:
   at least one metallic surface;
   a contacted optoelectronic semiconductor chip configured to emit radiation; and
   a protective layer arranged on the at least one metallic surface,
   wherein the protective layer comprises a protective material of at least one N-heterocyclic carbene, and wherein a covalent bond is formed between the protective material and the at least one metallic surface.

2. The optoelectronic component according to claim 1, wherein the protective layer is formed as self-assembled monolayer.

3. The optoelectronic component according to claim 2, wherein the protective layer has a layer thickness equal to or less than 1 nm.

4. The optoelectronic component according to claim 1, wherein the protective material is at least one N-heterocyclic carbene,
wherein the N-heterocyclic carbene is selected from the group consisting of

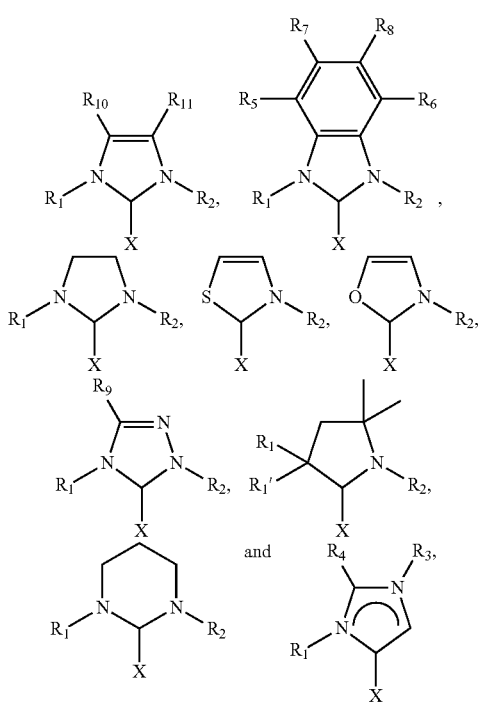

wherein $R_1$, $R_1'$, $R_2$, $R_3$, $R_4$, $R_5$, $R_6$, $R_7$, $R_8$, $R_9$, $R_{10}$ and $R_{11}$ are selected independently from one another of hydrogen, alkyl groups, alkoxy groups, groups with amines, amides, esters, carbonates, substituted or unsubstituted aromatic compounds, substituted or unsubstituted hetero-aromatic compounds, halogens or pseudo-halogens, and wherein —X is a covalent bond to the metallic surface.

5. The optoelectronic component according to claim 1, wherein the protective material is selected from the group consisting of

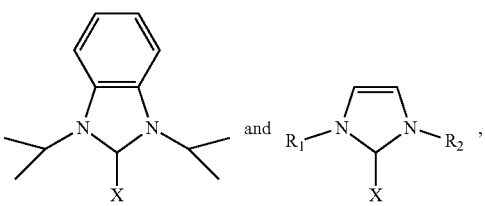

wherein $R_1$ and $R_2$ are in each case an alkyl-substituted phenyl, or

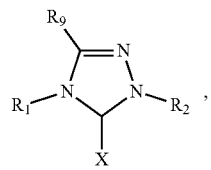

wherein $R_1$, $R_2$ and $R_9$ are in each case a phenyl, and wherein —X is a covalent bond to the metallic surface.

6. The optoelectronic component according to claim 1, wherein the metallic surface comprises a surface of a first metallic connecting contact, of a second metallic connecting contact, of a lead frame, of a bond pad or of a bond wire, and wherein the metallic surface includes at least one metal or alloy selected from silver, aluminum, cadmium, barium, indium, magnesium, calcium, lithium or gold.

7. The optoelectronic component according to claim 1, wherein all metallic surfaces of the optoelectronic component are covered with the protective layer in a form-fit manner.

8. The optoelectronic component according to claim 1, wherein the contacted optoelectronic semiconductor chip is arranged in a housing having a recess, wherein the metallic surface of the optoelectronic component includes at least the metallic surfaces of a bond pad, of a bond wire and of a lead frame, wherein the protective layer covers the metallic surfaces of the optoelectronic component within the recess in a form-fit manner, and wherein the recess is potted with a potting material including silicone.

9. The optoelectronic component according to claim 1, wherein the protective layer is diffusion-resistant toward corrosive gases.

10. A method for producing the optoelectronic component having at least one metallic surface according to claim 1, the method comprising:
providing the contacted optoelectronic semiconductor chip;
providing the at least one metallic surface; and
applying the protective layer on the at least one metallic surface so that the at least one N-heterocyclic carbene is a monolayer.

11. The method according to claim 10, wherein applying the protective layer on the at least one metallic surface comprises applying the protective layer by a vapor deposition.

12. The method according to claim 10, wherein applying the protective layer on the at least one metallic surface comprises applying the protective layer by wet-chemical processes.

13. The method according to claim 10, further comprising after applying the protective layer, potting the contacted optoelectronic semiconductor chip and the metallic surface coated with the protective layer.

14. The method according to claim 13, wherein potting is performed with silicone.

* * * * *